United States Patent [19]

Asmussen et al.

[11] 4,254,099
[45] Mar. 3, 1981

[54] PHARMACEUTICAL TABLET COMPOSITION

[75] Inventors: Bodo Asmussen, Ammersbek; Georg A. Ulex, Moorrege, both of Fed. Rep. of Germany

[73] Assignee: Beiersdorf Aktiengesellschaft, Hamburg, Fed. Rep. of Germany

[21] Appl. No.: 80,900

[22] Filed: Oct. 1, 1979

[30] Foreign Application Priority Data

Oct. 18, 1978 [DE] Fed. Rep. of Germany ....... 2845326

[51] Int. Cl.$^3$ ..................... A61K 9/20; A61K 31/705; A61K 47/00
[52] U.S. Cl. ........................................ 424/23; 424/19; 424/21; 424/22; 424/80; 424/182; 424/357; 424/361
[58] Field of Search .................................. 424/19–22, 424/23, 80, 182, 357, 361

[56] References Cited

U.S. PATENT DOCUMENTS

| | | | |
|---|---|---|---|
| 2,038,694 | 4/1936 | Wiggins | 424/23 |
| 2,698,822 | 1/1955 | Halpern et al. | 424/182 |
| 2,820,741 | 1/1958 | Endicott et al. | 424/80 |
| 2,857,313 | 10/1958 | Cooper et al. | 424/357 |
| 3,034,911 | 5/1962 | McKee et al. | 424/361 |
| 3,101,299 | 8/1963 | Ferrand | 424/357 |
| 3,148,124 | 9/1964 | Gaunt | 424/22 |
| 3,400,197 | 9/1968 | Lippmann | 424/21 |
| 3,424,842 | 1/1969 | Nurnberg | 424/94 |
| 3,632,778 | 1/1972 | Sheth et al. | 424/80 |
| 3,696,091 | 10/1972 | Eberlein et al. | 424/182 |
| 3,725,556 | 4/1973 | Hanssen et al. | 424/357 |
| 3,884,905 | 5/1975 | Bodor | 424/182 |
| 3,908,003 | 9/1975 | Horsh | 424/357 |
| 3,923,969 | 12/1975 | Baukal et al. | 424/19 |
| 3,929,996 | 12/1975 | Higuchi | 424/182 |
| 3,946,110 | 3/1976 | Hill | 424/230 |
| 4,013,785 | 3/1977 | Weintraub et al. | 424/357 |
| 4,021,546 | 5/1977 | Bodor | 424/182 |
| 4,143,129 | 3/1979 | Marsden | 424/80 |
| 4,147,768 | 4/1979 | Shaffer et al. | 424/182 |
| 4,151,273 | 4/1979 | Riegelman et al. | 424/182 |

FOREIGN PATENT DOCUMENTS 1239881 7/1971 United Kingdom ..................... 424/182

OTHER PUBLICATIONS

Yang et al., J. Pharm. Sci. 1979 68(5):560–565 (1979), C.A. 91 #44452g Aug. 6, 1979.
Gueurten et al., J. Pharm. Belg. 1978 33(3):189–193, C.A. 89 #204131r (1978), Dec. 11, 1978.
Flasch, H. et al., Arzneim, Forsch (1978), 28(2):326–330, C.A. 88 #197534y Jun. 26, 1978, Enhanced Bioavailability of Digoxin from Silica Matrix Formulations.
Khalil, S. Indian J. Pharm. Sci. (1978), 40(4):109–112, C.A. 89 #169012d Nov. 13, 1978.
Johansen, H. J. Pharm. Sci (1978), 67(1):134–136, C.A. 88 #110456c, Apr. 17, 1978.
Shah, N. et al., J. Pharm. Sci. (1974), 63(3):339–344, C.A. 80 #149066k (1974).
Ampolsuk et al. J. Pharm. Sci. (1974), 63(1):117–118, C.A. 80 #63811n (1974).

Primary Examiner—Shep K. Rose
Attorney, Agent, or Firm—Bierman & Bierman

[57] ABSTRACT

A pharmaceutical tablet composition for oral administration is disclosed which provides for accelerated release <> of a finely divided active ingredient contained therein which is only slightly soluble < in the gastrointestinal tract of a warm-blooded animal >. The tablet composition is characterized as containing a micro-dispersed, amorphous, porous silica having a primary particle size of between about 1 and 15 μm, a BET surface of between about 350 and 450 m$^2$/g, and a pore volume of between about 1.4 and 1.7 ml/g. A method of producing the tablet composition is also disclosed.

17 Claims, No Drawings

PHARMACEUTICAL TABLET COMPOSITION

BACKGROUND OF THE INVENTION

The present invention relates to drug tablets for oral administration which are adapted to facilitate dissolution of active ingredients which are only slightly soluble in the gastrointestinal tract of warm blooded animals. This results in a substantial increase in the active ingredients biological availability as compared to conventional tablet-formulations. Increased biological availability is of significant importance when dealing with slightly-soluble, high-potency drugs since it provides an opportunity to reduce the daily dosage necessary to produce the desired result.

More specifically, cardiotonic glycosides, such as digoxin and beta-acetyl digoxin are known to be resorbed in the upper regions of the small intestine. Generally, the resorbed quantity of the glycoside is smaller than the quantity of the active ingredient originally ingested.

This resorption loss is due, in part, to the physicochemical properties of the glycosides as they react with the resorption mechanism of the intestinal mucosa. However, the resorption loss is also due to the form of administration of the active ingredient. More specifically, maximum utilization of resorptive activity of the upper regions of the intestine can only take place when the above-mentioned glycosides exist in solution while present in the duodenum. In other words, undissolved cardiotonic glycosides which pass through the upper intestinal sections are not resorbed as part of the ingested dose thus reducing the biological availability of the active ingredient. Additionally, incomplete resorption results in major fluctuations in the amount of glycoside which, in view of the narrow desirable range of such substances in the body, can be undesirable and even hazardous.

The basic precondition for dissolution of a cardiotonic glycoside given orally in tablet form is disintegration of the tablet upon contact with the gastrointestinal fluid. Once disintegration of the tablet takes place into the primary particles of the compacted mass, the incorporated active ingredients are released and are then available to the dissolution process. The glycoside particles must then dissolve as quickly and as completely as possible to satisfy the requirement of good biological availability.

The rate of dissolution of active ingredients in tablet form can be improved by various known pharmaceuticaltechnological processes such as the addition of solubilizers, embedding in soluble polymers where a moleculardispersed state of the active ingredient is sought (so-called solid solution), and micronization of the active ingredient.

Compared with conventional methods of producing tablets, these methods generally increase production costs. Additionally, when solubilizers and polymeric auxiliary substances are used, problems arise concerning toxicological aspects, and also problems of chemical stability and compatibility between active and auxiliary substances. Obviously, these problems result in an increase in production costs as well.

The object of the present invention is to develop a new galenical tablet composition for slightly soluble active substances, preferably cardiotonic glycosides and, in particular, digoxin, which insures rapid and quantitative dissolution of the active substance upon contact with gastrointestinal fluid thereby providing greater biological availability than can be achieved with conventional tablets.

Another object is to find a production process which requires less expense than the aforementioned known procedures.

SUMMARY OF THE INVENTION

The subject of the invention, therefore, is a tablet which provides accelerated release of slightly soluble active ingredients contained therein in the gastrointestinal tract after oral administration. The tablet composition contains the active ingredient precipitated in finely divided form and fixed (absorbed) on micro-dispersed, amorphous, porous silica having a primary particle size of 1 to 15 $\mu$m, a BET surface of 350 to 450 m$^2$/g, and a pore volume of 1.4 to 1.7 ml/g.

The effective principle of the new drug form consists technologically in that the fixed active ingredient precipitated on the silica surface in the dissolved state in finely dispersed form (e.g. digoxin) is desorbed quickly and completely upon contact with water. This process can be interpreted in the sense of a displacement reaction, which is rendered possible by the high affinity of the silica surface to water facilitating entry of the active ingredient into solution with multiple oversatuation. More specifically, the new tablet provides short disintegration times (maximum of 15 seconds) measured in water at room temperature.

The required quantity of micro-dispersed, amorphous, porous silica having a primary particle size of 1 to 15 $\mu$m, a BET surface of between about 350 and 450 m$^2$/g, and a pore volume of 1.4 and 1.7 ml/g, having a SiO$_2$-content of 99.4%, depends on the quantity of active ingredient to be absorbed. Generally, the quantity ratio between active ingredient and silica is a maximum of 1:300. In addition, insufficient flow properties are observed when too much silica is used, whereby compactability to produce tablets is prevented or greatly hindered.

From this, the tablet silica content, based on the total quantity of tablet constituents, should not exceed 30 wt.%, preferably a maximum of 15 wt.%. When cardiotonic glycoside tablets are prepared, the desired range is 7 to 10 wt.%.

In order to insure proper molding composition properties, the present amount of silicea, containing the active ingrediant should be fixed with a tablet excipient, preferably lactose, in an amount between 70 and 80 wt.% based on the total weight.

The present tablets can be produced by a process characterized in that the silica is added in small portions under stirring to a solution of the active ingredient in a volatile organic solvent which is miscible with water. The resulting mixture, while still moist, is processed by a known wet-granulation method together with tablet excipients and watersoluble binders to form a granulated product. After drying, said product is compacted in the usual manner in the presence of known disintegrants and lubricants to form tablets.

The volatile organic solvents miscible with water are those which can readily be removed upon drying the mass. For example, alkanols such as methanol, ethanol or isopropanol, which are used with addition of water in the form of alkanol-water mixtures (e.g. in the form of an isopropanol-water mixture in the ratio 7:3) are preferably employed.

The water-soluble binder is advantageously charged in a quantity of 0.1 to 4 wt.% and, preferably, in a quantity of 0.7 to 1.5 wt.%, based on the total quantity of tablet constituents. The most preferred water-soluble binder is polyvinyl pyrrolidone. The disintegrants and lubricants of the usual kind (pelletizing aids) are charged in a total quantity of 5 to 15 wt.%. Preferred members of these respective groups include corn starch, swelling starch, and magnesium stearate or stearic acid. The compacting of the dried granulated product to tablets is effected in the usual manner under the usual pressure, depending on the type of machine. The hardness of the tablets should preferably be 15 to 40 N (determined by the Scheleuniger hardness tester).

PREFERRED EMBODIMENTS

The following examples are for illustrative purposes only and are not meant to limit the present invention as described in the appended claims.

EXAMPLE 12.5 g digoxin and 50.5 g polyvinyl pyrrolidone (MGW: 25000) in 1500 g of an isopropanol-water mixture (7+3) were added to the pot of a planetary agitator of a volume of 20 liters. 437 g of amorphous, porous silica are added in portions to this solution while stirring with a blade agitator. After the silica has combined with the liquid phase and the batch has taken on a gel type, completely lump-free structure, 4500 g of lactose are added in portions and the batch is mixed vigorously. The pasty mass is then spread evenly on drying trays and dried for 3 hours at 80° C. Thereafter the dry material is passed through a 0.75 mm screen, provided with an addition of 15 wt. % of pelletizing aids, and compacted to tablets in the usual manner.

The efficiency of the new tablet preparations was examined in vitro and in vivo on tablets containing 0.25 mg digoxin. The release behavior under standard conditions was determined by two different methods:

OVERSATURATION BEHAVIOR

Sufficient tablets to give 10 mg of digoxin are introduced into 50 ml of distilled water at 22° C. The same amount is also introduced at 22° C. into 50 ml of artificial intestinal juice. The latter is a phosphate buffer according to Münzel, Büchi and Schulz prepared by dissolving 3.56 grams of $Na_2HPO_4.2H_2O$ and 6.44 g $NaH_2PO_4.H_2O$ in 1000 ml distilled water. The resultant solution has a pH 6.5. In both cases, the tablets are shaken vigorously for 30 seconds and filtered immediately. The digoxin concentration in the filtrate is determined by spectrophotometry using the dixanthylurea method and calculated as mg digoxin/100 ml solvent.

LIBERATION IN THE FLOW CELL

In a flow cell with turbulent flow characteristics, as described more fully in DAS No. 2,504,166, a glycoside tablet is eluated with distilled water at 22° C. and a second tablet is eluated at 22° C. with artificial intestinal juice (as described above) at a volume flow of 40 ml/min. The eluate fractions obtained after flooding of the cell, in the periods 0-30, 30-60, and 60-90 seconds, are collected. The digoxin content is determined in the above-described manner and stated cumulatively in percent of the total active ingredient of the tablet.

In vivo, the bioavailability was determined on 12 normal adults averaging 36 years of age. Each subject received, in random sequence, 0.5 mg digoxin in tablet form and injected intravenously. There were intervals of at least 14 days between administrations. The bioavailability parameter was the renal digoxin elimination accumulated over 6 days. The digoxin determination was effected by radioimmunology (H. Flasch: "Klinische Wochenschrift" 53, 873–877 [1975]). The digoxin quantity eliminated after i.v. administration served as the standard for 100 percent bioavailability. In addition, for different maintenance doses of the new tablet preparation, the resulting digoxin plasma levels were checked in an open clinical study.

TEST RESULTS

The tests were carried out with tablets which, in a total weight of 115 mg, contained 100 mg silicalactose granulate and 15 mg pelletizing aids.

IN VITRO TESTS

The oversaturation and liberation behavior was examined for comparison also on tablets which contained 0.25 mg digoxin in the form of a lactose triturate.

TABLE 1.

| Oversaturation behavior/liberation in the flow cell | | |
|---|---|---|
| | Digoxin in new preparation form acc. to invention | Digoxin as lactose trituration pelletized |
| Disintegration time of the tablets measured in water, 22° C. (s) | 11 | 12 |
| Oversaturation behavior in water (22° C.) (mg digoxin/100 ml $H_2O$) | 18.8 (0.1,3) | 6.3 (0.1,3) |
| $\bar{x}$ (s,n) | | |
| Liberation behavior of the flow cell in water (22° C.) % active ingredient | | |
| 30s  $\bar{x}$ (s, n) | 86.1 (3.4,6) | 43.8 (0.8.3) |
| 60s | 92.9 (2.7,6) | 55.1 (0.6,3) |
| 90s | 94.8 (1.8,5) | 61.2 (0.5,3) |

The saturation concentration of digoxin in water at room temperature is 4 mg/100 ml. At equal tablet disintegration time, digoxin goes into solution from the new preparation form under standard conditions with significantly stronger oversaturation than from a conventional tablet. In the flow cell, digoxin is liberated clearly faster from the new formulation than from the lactose triturate tablet. Corresponding results are obtained when working with artificial intestinal juice.

These in vitro findings, which suggest an improvement of the bioavailability, were confirmed by in vivo tests.

IN VIVO TESTS

The bioavailability of the new tablet preparation according to the invention is 82% of the i.v. standard and thus is in the order of magnitude of the values found upon ingestion of aqueous-alcoholic solutions. By comparison, the bioavailabilities of commercial digoxin preparations in tablet form are stated to be 50–70%.

In an open clinical study, the relationship between the maintenance dose and digoxin plasma level was examined on 83 hospitalized digitalized patients with sound kidneys, of both sexes, under steady state conditions. The tablets used contained 0.1 mg digoxin in the new preparation form. In their excipient composition, they were identical to the tablets used in the in vitro tests and in the determination of the biological availability.

The tested maintenance doses and the respective digoxin plasma concentrations are stated in Table 2.

Table 2. Plasma level at different maintenance doses of digoxin, administered in the new galenical preparation form, according to the invention. Steady-state conditions.

| Maintenance dose (mg digoxin/day) | Digoxin plasma level (ng/ml) | $s_{\bar{x}}$ (ng/ml) | Number of Patients |
|---|---|---|---|
| 0.2 | 1.21 | 0.10 | 32 |
| 0.3 | 1.49 | 0.11 | 33 |
| 0.4 | 1.63 | 0.14 | 18 |

The digoxin plasma levels obtained with the new digoxin tablet preparation of the invention are significantly higher than plasma levels which are stated in the literature for comparable maintenance doses from conventional tablet preparations (Table 3).

Table 3. Plasma level at different maintenance doses of digoxin, administered with conventional tablet preparations. Steady-state conditions.

| Maintenance dose (mg digoxin/day) | Digoxin plasma level (*) (ng/ml) | Number of patients |
|---|---|---|
| 0.25 | 0.95 | 380 |
| 0.50 | 1.54 | 122 |

(*) Weighted average values. They were determined for each maintenance dose from the mean plasma levels of five kidney-sound patient groups.

From the above stated results of the comparative tests, the superiority of the tablet according to the present invention is clearly evident. The invention is to be broadly construed and not to be limited except by the character of the claims appended hereto.

We claim:

1. A pharmaceutical composition in tablet form for oral administration providing for accelerated release of digoxin contained therein comprising a microdispersed, amorphous, porous silica having a primary particle size of between 1 and 15 μm, a BET surface of between about 350 and 450 m²/g, and a pore volume of between about 1.4 and 1.7 ml/g having absorbed thereon said active ingredient in finely divided form.

2. The composition of claim 1 wherein said BET surface is between about 370 and 430 m²/g.

3. The composition of claim 1 wherein the weight ratio of said active ingredient to said silica is no greater than 1:300.

4. The composition of claim 1 wherein the weight ratio of said silica to said tablet is no greater than 30 weight percent.

5. The composition of claim 4 wherein said ratio is no greater than 15 weight percent.

6. The composition of claim 5 wherein said ratio is between about 7 and 10 weight percent.

7. The composition of claim 1 further comprising a pharmaceutically acceptable tablet excipient in an amount of between about 70 and 80 weight percent based on the total weight of said tablet.

8. The composition of claim 7 wherein said excipient is lactose.

9. The composition of claim 1 further comprising a water-soluble binder in an amount between about 0.1 and 4.0 weight percent based on the total weight of said tablet.

10. The composition of claim 9 wherein said amount is between about 0.7 and 1.5 weight percent.

11. The composition of claim 9 wherein said water-soluble binder is polyvinyl pyrrolidone.

12. The composition of claim 1 further comprising disintegrants and lubricants in an amount between about 5 and 15 weight percent based on the total weight of said tablet.

13. The composition of claim 12 wherein said disintegrants and lubricants are selected from cornstarch, swelling starch, magnesium stearate and stearic acid.

14. A process for the production of the composition of claim 1 comprising.
   (a) mixing said silica into a solution of said digoxin in the presence of a volatile organic solvent which is miscible with water to form a resulting mixture.
   (b) granulating said mixture while still moist to form a granulated product.
   (c) drying said granulated product, and
   (d) compacting said granulated product into tablets.

15. The process of claim 14 further comprising the steps of
   (a) granulating said resulting mixture in the presence of a pharmaceutically acceptable tablet excipient and a water-soluble binder and
   (b) compacting said granulated product in the presence of a disintegrant and a lubricant.

16. The process of claim 14 wherein said volatile organic solvent is an alkanol.

17. A pharmaceutical composition in tablet form for oral administration providing for accelerated release of digoxin contained therein comprising
   (a) up to 30 weight percent of a microdispersed, amorphous, porous silica having a primary particle size of between about 1 and 15 μm, a BET surface of between about 350 and 450 m²/g, and a pore volume of between about 1.4 and 1.7 ml/g, and having absorbed thereon said digoxin in finely divided form such that the weight ratio of said active ingredient to said silica is no greater than 1:300,
   (b) between about 70 80 weight percent of a pharmaceutically acceptable tablet excipient,
   (c) between about 0.1 and 4.0 weight percent of a water-soluble binder, and
   (d) between about 5 and 15 weight percent of disintegrants and lubricants based on the total weight of said tablet.

* * * * *